United States Patent [19]

Bly et al.

[11] Patent Number: 4,899,754
[45] Date of Patent: Feb. 13, 1990

[54] FLAT, CONFORMABLE, BIOMEDICAL ELECTRODE ALLOWING REMOVAL OF ELECTRICAL LEAD WIRE

[75] Inventors: Jerome G. Bly, Minneapolis, Minn.; Charles W. Roberts, North Hudson, Wis.

[73] Assignee: Minnesota Mining and Manufacturing Company, St. Paul, Minn.

[21] Appl. No.: 179,519

[22] Filed: Apr. 8, 1988

Related U.S. Application Data

[63] Continuation-in-part of Ser. No. 915,138, Oct. 3, 1986, Pat. No. 4,771,783, which is a continuation-in-part of Ser. No. 892,691, Aug. 1, 1986, Pat. No. 4,727,880.

[51] Int. Cl.$^4$ .......................... A61B 5/04; A61N 1/04
[52] U.S. Cl. .................................. 128/640; 128/798; 128/802
[58] Field of Search .............................. 128/639–641, 128/798, 802, 803

[56] References Cited

U.S. PATENT DOCUMENTS

| | | | |
|---|---|---|---|
| 3,993,049 | 11/1976 | Kater | 128/640 |
| 4,422,461 | 12/1983 | Glumec | 128/798 |
| 4,522,211 | 6/1985 | Bare et al. | 128/640 |
| 4,554,924 | 11/1985 | Engel | 128/640 |
| 4,653,501 | 3/1987 | Cartmell et al. | 128/640 |
| 4,657,023 | 4/1987 | Kuhn | 128/640 |
| 4,679,563 | 7/1987 | Wada et al. | 128/640 |
| 4,727,880 | 3/1988 | Roberts | 128/640 |
| 4,771,783 | 9/1988 | Roberts | 128/640 |

Primary Examiner—Lee S. Cohen
Attorney, Agent, or Firm—Donald M. Sell; Walter N. Kirn; William D. Bauer

[57] ABSTRACT

A biomedical electrode (10) adapted to be applied to a body, the biomedical electrode (10) having a surface area divided into a first zone (38), a second zone (40), and a third zone (42). The biomedical electrode (10) has a first layer of adhesive (24) which is electrically conductive and which is adapted to be applied to the body, a conductive layer (22) positioned adjacent the first layer of adhesive (24), a second layer of adhesive (16), and a protective, electrically insulative web (12) positioned adjacent the second layer of adhesive (16). The second layer of adhesive (16) holds the protective, electrically insulative web (12) to the conductive layer (22) in the third zone (42) of the biomedical electrode (10). A removable release liner (18) is positioned in the first zone (38) between the second layer of adhesive (16) and the conductive layer (22) preventing the protective, electrically insulative web (12) from sticking to the conductive layer (22) in the first zone (38) of the biomedical electrode (10). An insertable electrical lead wire (14) is insertable in the first zone (38) between the second layer of adhesive (16) and the conductive layer (22) upon removal of the removable liner (18). The protective, electrically insulative web (12) has an edge (44) in the second zone (40) which is easily grasped so that the protective, electrically insulative web (12) may be pulled and removed from the biomedical electrode (10) allowing removal of the electrical lead wire (14).

6 Claims, 5 Drawing Sheets

FLAT, CONFORMABLE, BIOMEDICAL ELECTRODE ALLOWING REMOVAL OF ELECTRICAL LEAD WIRE

RELATED APPLICATIONS

The present application is a continuation-in-part of United States patent application Ser. No. 06/915,138, filed Oct. 3, 1986, now U.S. Pat. No. 4,771,783 which is a continuation-in-part of U.S. patent application Ser. No. 06/892,691, filed Aug. 1, 1986, now U.S. Pat. No. 4,727,880.

BACKGROUND OF THE INVENTION

The present invention relates generally to biomedical electrodes.

Biomedical electrodes are useful for both stimulation and body monitoring functions. Stimulation uses of biomedical electrodes include transcutaneous electronic nerve stimulation (TENS) for the treatment of pain and neuromuscular stimulation (NMS) as, for example, treatment for scoliosis. Body monitoring uses for biomedical electrodes include electrocardiogram (ECG) for monitoring heart activity.

Among biomedical electrodes in existence are those of Phipps et al., Cartmell and Larimore. Phipps et al in U.S. Pat. No. 3,170,459 discloses a biomedical instrumentation electrode constructed from multiple plies of discs made from a relatively inflexible material, i.e., cork. The electrode utilizes a conductive gel to establish electrical contact with the body. Cartmell in U.S. Pat. No. 4,543,958 discloses a medical electrode assembly. The electrode has a flexible, dimensionally stable substrate which is striped with an electrically conductive paint. The electrode is then clamped into a bulky cable connector. Larimore in U.S. Pat. No. 4,458,696 (assigned to Minnesota Mining and Manufacturing Company) discloses a TENS electrode with a raised structure to permit entry of and attachment to a tubular electrical conductor.

These electrodes suffer from several deficiencies including that all are "high profile" electrodes and that the electrodes do not "conform" well to the body.

SUMMARY OF THE INVENTION

With a biomedical electrode such as is described in U.S. Pat. No. 4,727,880 and U.S. Ser. No. 06/915,138 (of which this application is a continuation-in-part), the electrode is applied to the body, the protective web is lifted at the spot of the removable release liner which is then removed, the electrical lead wire inserted and the protective web is placed over the electrical lead wire securing the lead wire in place. The biomedical electrode is now usable in its normal mode of operation. Electrical signals may be applied via the lead wire to the electrode which are then transmitted by the electrode to the body to which the electrode is applied or, alternatively, electrical signals from the body may be read by way of the electrode and the electrical lead wire. When use of the electrode in that situation is completed, it is desirable to remove the electrical lead wire from the electrode for reuse and to remove the remainder of the electrode from the body for disposal. Since the electrical lead wire is adhesively secured in the electrode with the protective web, it is difficult, if not impossible, to remove the electrical lead wire without first removing the covering of the protective web. Unfortunately in the electrodes described in the parent applications there is no readily available mechanism to allow the removal of the protective web.

Accordingly, the biomedical electrode of the present invention is constructed similarly to the electrodes described in the parent applications but further has features which readily allow the grasping of an edge of the protective web so that the protective web may be pulled to reveal the electrical lead wire and allow the removal and reuse of the electrical lead wire. It is preferred that the edge to be grasped be opposite from the side of the protective web from which the removable release liner is removed. It is preferred that the surface area of the biomedical electrode be divided into three zones as will hereafter be described in order to facilitate easy access to both the release liner an the edge to be grasped to remove the protective web.

The present invention then provides a biomedical electrode which is (1) flatter and more conformable, (2) has a very low profile, (3) may be trimmed to differing shapes, (4) has flexibility in lead wire insertion direction, and (5) allows ease of removal of the electrical lead wire following use of the biomedical electrode so that the electrical lead wire may be reused. The electrode of the present invention is flatter and more conformable to body contours and body movement than prior electrodes. The electrode relies on an adhesive contact with a flat electrical conductor as opposed to rubber connector strips or snaps. The electrode has a very low profile which makes it suitable to be worn under tight clothing and to be comfortable when slept upon or when leaned against, as, for example, when sitting in a chair. The electrode may be trimmed to virtually any size or shape to allow adaptability in placement and location. The electrode allows for flexibility in lead wire insertion and allows for the lead wire to be inserted from the end of the electrode or from either side. The reuseability of the lead wire leads to economy for use of the biomedical electrode. However, with some other biomedical electrodes it may be extremely difficult to actually remove the electrical lead wire from the biomedical electrode due to the adhesives involved and the degree to which the end of the electrical wire is secured. The present invention solves this problem by providing a zone in the biomedical electrode into which the electrical lead wire is inserted and a zone which facilitates the grasping and removal of the protective web allowing the easy removal of the electrical lead wire. The facility for grasping of the protective web in that zone may be provided by a portion which is uncoated by adhesive, by folding over the adhesive coated protective web, by coating the adhesive with a substance which renders the adhesive nonsticky, or other similar means. It is possible to further improve the ease with which that portion is grasped for removal by scalloping the edge.

The present invention provides a biomedical electrode adapted to be applied to a body, the electrode having a surface area divided into a first zone, a second zone, and a third zone, which in a preferred embodiment is intermediate the first zone and the second zone. The biomedical electrode has a first layer of adhesive which is electrically conductive and which is adapted to be applied to the body, a conductive layer positioned adjacent the first layer of adhesive, a second layer of adhesive, and a protective, electrically insulative web positioned adjacent the second layer of adhesive. The second layer of adhesive holds the protective, electrically insulative web to the conductive layer in the third zone of the electrode. A removable release liner is positioned in the first zone between the second layer of adhesive and the conductive layer preventing the protective, electrically insulative web from sticking to the conductive layer in the first zone of the electrode. An insertable electrical lead wire having a distal uninsulated portion and a proximate insulated portion is insertable in the first zone between the second layer of adhesive and the conductive layer upon removal of the removable liner. The protective, electrically insulative web has an edge in the second zone which is easily grasped so that the protective, electrically insulative web may be pulled and removed from the electrode allowing removal of the electrical lead wire.

In one embodiment, the edge is formed by having a portion of the protective, electrically insulative web uncoated by the second layer of adhesive. In another embodiment, the edge is spaced from the outside perimeter of the electrode. In another embodiment, the edge is scalloped to permit easier grasping. In another embodiment, a portion of the protective, electrically insulative web forms the edge by being folded over in the second zone of the electrode. In another embodiment, the edge is formed by covering the second layer of adhesive over a portion of the second zone with a substance resulting in a nonsticky surface. In another embodiment, the nonsticky surface of the protective, electrically insulative web has a scalloped edge to permit easier grasping. In another embodiment, a third layer of adhesive which is electrically conductive is positioned between the electrically conductive layer and the release liner over another portion of the surface of the biomedical electrode where the distal end of the insertable electrical lead wire is adapted to be placed. In another embodiment, the protective, electrically insulative web is discontinuous in the second zone being composed of a first part covering the first and third zones and a portion of the second zone and of a second part covering a portion of the second zone, the first part of the protective, electrically insulative web having the edge.

The present invention also provides a biomedical electrode adapted to be applied to a body, having a first layer of adhesive which is electrically conductive and which is adapted to be applied to the body, a conductive layer positioned adjacent the first layer of adhesive, a second layer of adhesive, and a protective, electrically insulative web positioned adjacent the second layer of adhesive. The second layer of adhesive holds the protective, electrically insulative web to the conductive layer. A removable release liner is positioned over a portion of the surface area of the biomedical electrode between the second layer of adhesive and the conductive layer preventing the protective, electrically insulative web from sticking to the conductive layer over the portion of the surface area of the electrode. An electrical lead wire having a distal uninsulated portion and a proximate insulated portion is inserted between the second layer of adhesive and the conductive layer upon removal of the removable liner. The protective, electrically insulative web has an edge which is easily grasped so that the protective, electrically insulative web may be pulled and removed from the electrode allowing removal of the insertable electrical lead wire.

BRIEF DESCRIPTION OF THE DRAWINGS

The foregoing advantages, construction and operation of the present invention will become more readily apparent from the following description and accompanying drawings in which.

DETAILED DESCRIPTION OF THE PREFERRED EMBODIMENTS

Figure 1:
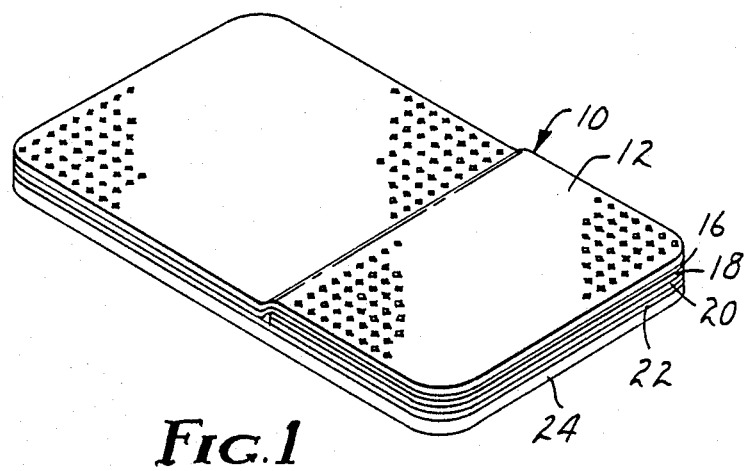
FIG. 1 is a isometric view of a biomedical electrode.

FIG. 1 illustrates an isometric view of a biomedical electrode 10. The biomedical electrode 10 is also shown in expanded side view of FIG. 2, The top of the biomedical electrode 10 is a protective, electrically insulative web 12. Web 12 protects the top of biomedical electrode 10 from physical damage and covers lead wire 14 when it is inserted in the biomedical electrode 10 to help secure lead wire 14 in place. Web 12 is electrically insulative to confine the electrical signals used in the biomedical electrode to the lead wire 14 or to the body (not shown). As shown in FIG. 1, web 12 is preferably perforated making web 12 more conformable to the body contour and for esthetics. The perforations also assist in the tearability of web 12 once it is desired to remove lead wire 14 from the biomedical electrode 10. It is preferred that web 12 is approximately 4 mils (1.0 millimeters) thick and is constructed from a pigmented low molecular weight polyethylene film. Web 12 is attached to the remainder of biomedical electrode 10 with a pressure sensitive adhesive 16. It is preferred that the pressure sensitive adhesive 16 be an acrylate adhesive. A release liner 18, which is removable, is placed beneath pressure sensitive adhesive 16 covering a portion of the surface area of biomedical electrode 10. Release liner 18 facilitates the lifting of web 12 away from the remainder of the biomedical electrode 10 in order that lead 14 may be inserted and web 12 subsequently reapplied securing lead wire 14 in biomedical electrode 10. It is preferred that the release liner 18 be a Polyslick ™ material as manufactured by James River Corporation, H. P. Smith Division, Bedford Park, Ill. A conductive adhesive 20 is positioned in the biomedical electrode 10 below release liner 18. Conductive adhesive 20 need only cover a portion of the surface area of biomedical electrode 10 to which lead wire 14 may be positioned. It is preferred that the conductive adhesive 20 cover approximately the same surface area of biomedical electrode 10 as does release liner 18. This allows for relative general ease in the positioning of lead wire 14 once release liner 18 has been removed. It is also preferred that the conductive adhesive 20 be made conductive through the inclusion of silver particles. It is preferred that a resistivity measurement using a one inch square brass plate above and below the adhesive measures approximately 0.01 ohms. The exact conductivity of conductive adhesive 20, of course, depends upon the end use to which biomedical electrode 10 in intended. Generally, it is expected that resistivities of conductive adhesive may generally range up to one ohm. Alternatively, approximately ten ohms may be sufficient and higher resistivities may be allowable in other embodiments and for other uses for biomedical electrode 10. Conductive adhesive, especially conductive adhesives containing silver particles are widely available. An example of a suitable adhesive is a solvent based acrylate adhesive containing silver particles about 3 mils (0.76 mm) in diameter which is coated through a knife coater at about 12 mils (3.05 mm) thickness. The coated adhesive is heated to drive off the solvent resulting in an adhesive layer of about 1.0 mils (0.38 mm) in thickness. Note that the silver particles are larger than the thickness of the resulting adhesive giving the layer is needed electrical conductivity. An adhesive similar to this but which has been coated on aluminum is available as X1170 foil tape from Minnesota Mining and Manufacturing Company, St. Paul, Minn. Below conductive adhesive 20 an electrically conductive film 22, preferably a metal vapor coated conductive film, covers a large portion of the surface area of biomedical electrode and, in a preferred embodiment, covers the entire surface of biomedical electrode 10. The purpose of electrically conductive film 22 is to disburse the current delivered by or received by biomedical electrode 10 over a larger portion of the surface area of biomedical electrode 10. Electrically conductive film 22 may also operate to provide an ion barrier between the insertable lead wire 14 and the body. In a preferred embodiment, the electrically conductive film is an ethylene vinyl acetate loaded with approximately 28% carbon or a, Velostat ® film manufactured by Minnesota Mining and Manufacturing Company, Saint Paul, Minn. in either case coated top side with $7 \times 10^{-8}$ to $1.2 \times 10^{-7}$ meters thick vapor coat of aluminum or silver. It is preferred that electrically conductive film 22 be approximately 3 mils (0.76 millimeters) thick. As indicated, conductive adhesive 24 operates to secure biomedical electrode 10 to the body to biomedical electrode 10 or visa versa. It is preferred that conductive adhesive 24 have better cohesion than adhesion in order to facilitate the ease in which the biomedical electrode 10 may be removed from the body. Conductive adhesive 24 may generally have a volume resistivity of the range from 50 to 200 ohm-centimeters although lower and high volume resistivities may work for some uses of the biomedical electrode 10. It is preferred that conductive adhesive 24 be from 10 mils (2.5 millimeters) to 60 mils (15.2 millimeters) thick. In a reuseable electrode it is preferred that the conductive adhesive 24 be from 30 mils (7.6 mm) to 44 mils (11.2 mm) thick. In a disposable electrode it is preferred that the conductive adhesive be from 10 mils (2.5 mm) to 24 mils (6.3 mm) thick. An example of a conductive adhesive ≧desirable for a reuseable electrode is described in U.S. Pat. No. 3,865,770, Blake, Water-Dispersable Pressure-Sensitive Adhesive Tape Made Therewith, and Novel Tackifiers Therefor, which is hererby incorporated by reference. In one embodiment, the adhesive in Blake is modified and the following ingredients used:

| Ingredient | Dry Weight Grams | Dry Weight Percent |
|---|---|---|
| Copolymer: Butyl Acrylate & Acrylic Acid in 3:1 ratio | 83.177 | 40.945 |
| Glycerin | 20 | 9.8452 |
| Butanediol | 20 | 9.8452 |
| Sorbitol | 20 | 9.8452 |

-continued

| Ingredient | Dry Weight Grams | Dry Weight Percent |
|---|---|---|
| Methyl diethanolamine (MDEA) | 28 | 13.783 |
| Potassium Chloride (KCl) | 6.9678 | 3.4300 |
| Foral AZ (hydrogenated wood rosin) | 25 | 12.306 |
| TOTAL | 203.14 | 100.04 |

An example of a conductive adhesive 24 desirable for a disposable electrode is described in U.S. Pat. No. 4,554,924, Engel, Conductive Adhesive and Biomedical Electrode, which is hereby incorporated by reference. In one embodiment, the adhesive in Engel is modified and the following ingredients be used:

| Ingredient | Dry Weight Grams | Dry Weight Percent |
|---|---|---|
| 1,4 Butanediol | 45 | 6.3993 |
| Glycerin | 75 | 10.665 |
| Sorbitol | 290 | 41.240 |
| K739, Polyacrylic | 17 | 2.4175 |
| Potassium Hydroxide | 3.25 | 0.46217 |
| Total Water | 155 | 22.042 |
| Acrylic Acid | 115 | 16.354 |
| Irgacure | 0.51635 | 0.07343 |
| Tegbm | 2.3186 | 0.32972 |
| Methyl ethyl hydroquinone | 0.12 | 0.01706 |
| TOTAL | 703.20 | 100.04 |

The preferred electrically conductive adhesive 24 is comprised of the following ingredients:

| Ingredient | Dry Weight Percent |
|---|---|
| Copolymer: | |
| Acrylic Acid | 10.00 |
| N—vinyl pyrrolidone | 10.00 |
| Glycerin | 50.88 |
| Guar gum | 0.12 |
| Water | 26.00 |
| Sodium hydroxide | 2.80 |
| Irgacure | 0.07 |
| TEGBM | 0.125 |
| | 100.00 |

Optionally, a second release liner (not shown) may be provided below conductive adhesive 24 to facilitate transportation and storage of biomedical electrode 10 before use or between uses.

Biomedical electrode 10 may be utilized by applying the biomedical electrode 10 to a body being secured by conductive adhesive 24. The protective, electrically insulative web 12 may be lifted since release liner 18 prevents the protective, electrically insulative web 12 from sticking to conductive adhesive 20. Once the protective insulative web 12 is lifted, release liner 18 may be removed and discarded. At this time, lead wire 14 may be inserted so that noninsulated portion 26 of lead wire 14 is positioned over conductive adhesive 20. Lead wire 14 also has an insulative portion 28 which extends from beneath the confines of protective, electrically insulative web 12 and may be connected to suitable electronic equipment intended to utilize biomedical electrode 10. Lead wire 14 may be a copper wire whose insulated portion 28 is insulated with any suitable insulation, as, for example, rubber or plastic. The end of noninsulated portion 26 of lead wire 14 is a flat crimped on conductor plate 30. Conductor plate 30 is flat which facilitates the biomedical electrode 10 being of low profile, flat and conformable to the body. Conductor plate 30 may, for example, be a zinc plated copper or, optionally, a silver plated copper with a chloride treatment, or, preferably nickel coated brass.

Figure 2:
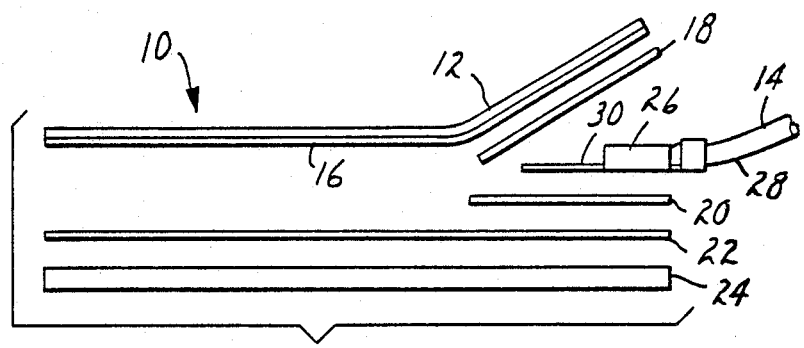
FIG. 2 is a side view of the biomedical electrode of FIG. 1.
Figure 3:
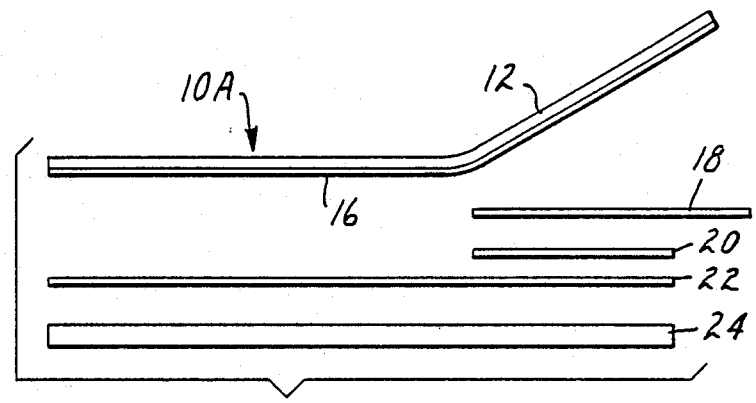

FIG. 3 illustrates an alternative embodiment for the biomedical electrode 10A of the present invention. The construction of the biomedical electrode 10A in FIG. 3 is similar to the biomedical electrode 10 in FIG. 2 except that protective, electrically insulative web 12, pressure sensitive adhesive 16 and release liner 18 extend from one edge of conductive adhesive 20, electrically conductive film 22 and conductive adhesive 24. Having these items extend beyond the edge facilitates the lifting of protective, electrically insulative web 12 in order that release liner 18 may be removed and lead wire 14 inserted.

Figure 4:
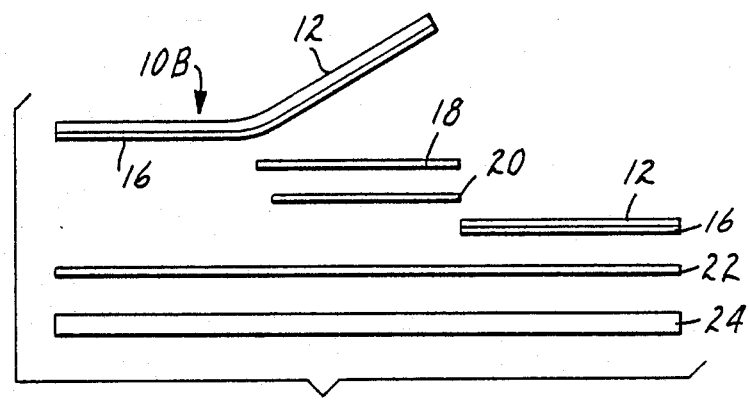
FIGS. 3, 4, 5, 6, 7 and 8 are side views of alternative embodiments of biomedical electrodes.

FIG. 4 illustrates another expanded side view of another embodiment of the biomedical electrode 10B of the present invention. The embodiment illustrated in FIG. 4 is similar with that as biomedical electrode 10 illustrated in FIG. 2 with the exception that the portion of the surface area of biomedical electrode 10 which is covered by release liner 18 and conductive adhesive 20 is positioned centrally in the biomedical electrode 10. This embodiment illustrates that protective insulative web 12, as well as pressure sensitive adhesive 16 may be separated into two portions. Biomedical electrode 10B as illustrated in FIG. 4 operates as before, protective insulative web 12 is lifted, release liner 18 is removed and lead wire 14 is inserted over conductive adhesive 20.

In the embodiments of biomedical electrode illustrated in FIGS. 1–4, a single sheet release liner 18 is illustrated. In these embodiments, release liner 18 is coated both sides with a release agent allowing the release liner 18 to release both from pressure sensitive adhesive 16 and conductive adhesive 20.

Figure 5:
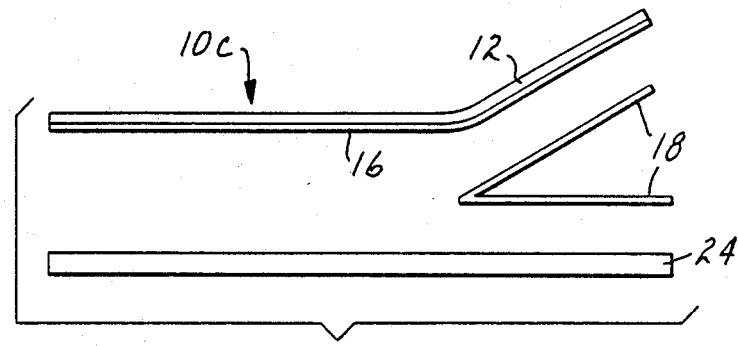

Another embodiment of biomedical electrode 10C is illustrated in a side exploded view in FIG. 5. The biomedical electrode 10C illustrated in FIG. 5 also contains a protective, electrically insulative web 12 and a pressure sensitive adhesive 16. The biomedical electrode 10 also contains a release liner 18. Release liner 18 is illustrated as being folded with the closed side fold being positioned interiorly with respect to biomedical electrode 10 and the open side fold being positioned near an edge of the protective, electrically insulative web 12. The release liner 18 as illustrated in FIG. 5 may be coated on only one side, the outside of release liner 18 as it is folded so that the release agent still contacts pressure sensitive adhesive 16 and conductive adhesive 24. As in the other embodiments, the biomedical electrode 10C illustrated in FIG. 5 contains conductive adhesive 24 preferably along the entire bottom surface area of biomedical electrode 10. Conductive adhesive 24 is the same as and performs the same purpose as conductive adhesive 24 in FIGS. 1–4. Note that the biomedical electrode 10C illustrated in FIG. 5 is missing electrically conductive adhesive 20 and electrically conductive film 22. As noted earlier, electrically conductive film 22 was used to facilitate the dispersion of electrical currents over the entire surface of biomedical electrode. In situations where such dispersion is not required or such dispersion is not required to be achieved as well as can be achieved with the electrically conductive film 22, the electrically conductive film 22 may be omitted. With the omission of electrically conductive film 22, electrically conductive adhesive 20 is also no longer needed. Electrically conductive adhesive 20 was utilized to secure lead wire 14 when it was positioned within biomedical electrode 10. With the embodiment of the biomedical electrode 10C illustrated in FIG. 5 when release liner 18 is removed, lead wire 14 may be inserted in its place and is secured between protective insulative web 12 by pressure sensitive adhesive 15 and conductive adhesive 24.

Figure 6:
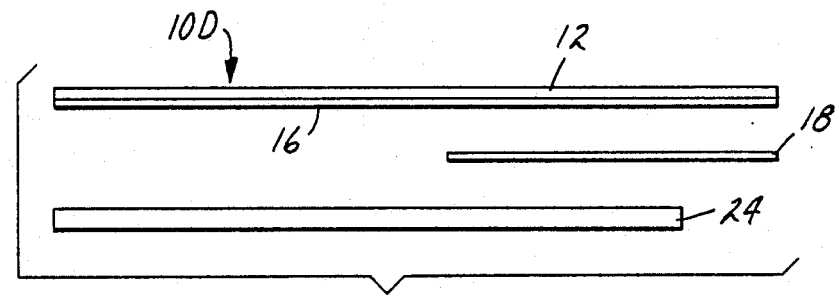

The biomedical electrode 10D as illustrated in FIG. 6 is constructed similarly to the embodiment of biomedical electrode 10C illustrated in FIG. 5 with the exception being that protective insulative web 12, pressure sensitive adhesive 15 and release liner 18 extend beyond an edge of conductive adhesive 24 (as in FIG. 3) to facilitate lifting of protective insulative web 12 and removal of release liner 18.

Figure 7:
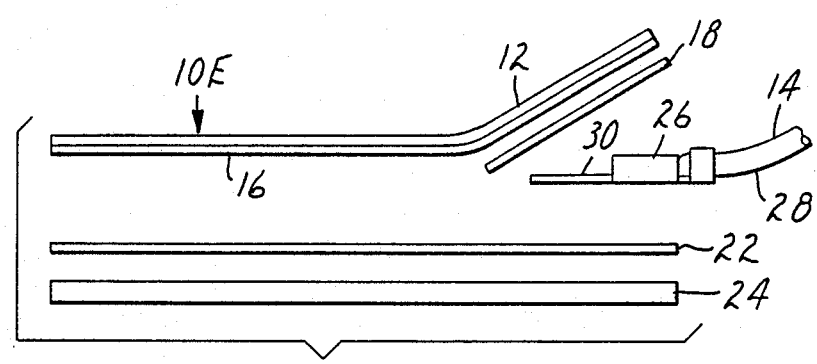

The biomedical electrode 10E illustrated in FIG. 7 is similar to the biomedical electrode 10 illustrated in FIG. 2. Biomedical electrode 10E omits electrically conductive 20 (shown in FIG. 2) and since electrically conductive adhesive 20 has been omitted release liner 18 need only be release coated on the side facing adhesive 16. As in FIG. 2, the biomedical electrode 10E of FIG. 6 has a protective, electrically insulative web 12 which is secured to the remainder of the biomedical electrode 10E with a layer of adhesive 16. It is preferred that layer of adhesive 16 be a pressure sensitive adhesive. As stated above, release liner 18 covers a portion of the surface area of layer of adhesive 16 and is release coated at least on its top side facing layer of adhesive 16. An electrically conductive film 22 is positioned below both adhesive 16 and release liner 18. It is preferred that electrically conductive film be a metallic coated electrically conductive substrate such as an aluminum vapor coat of from 200 to 1200 angstroms thick on a 28% carbon loaded ethylene vinyl acetate substrate. The metallic vapor coat should be on the top side of the electrically conductive film 22 facing said release liner 18. Generally, the electrical resistance over the length of the electrically conductive film should be less than or equal to 1 ohms per inch (0.39 ohms per centimeter) of electrically conductive film 22. An electrically conductive adhesive 24 of the same as described with respect to FIG. 2, is than located below electrically conductive film 22 opposite the release liner 18 or layer of adhesive 16. Optionally, a second release liner (not shown) may be then applied to electrically conductive adhesive 24. The electrode is utilized by after first removing the release liner from electrically conductive adhesive 24 if any, applying the biomedical electrode to the body with electrically conductive adhesive 24. Protective web 12 may then be lifted and release liner 18 removed. Lead wire 14 is then inserted into the location where release liner 18 was removed and protective web 12 is secured over lead wire 14. The conductor plate 30 part of the noninsulated portion 26 of lead wire 14 is held in place by adhesive 15 and makes electrical contact with electrically conductive film 22. Insulative portion 28 of lead wire 14 is contained under the edge of protective web 12 in order to have a completely insulated biomedical electrode 10E system.

Figure 8:
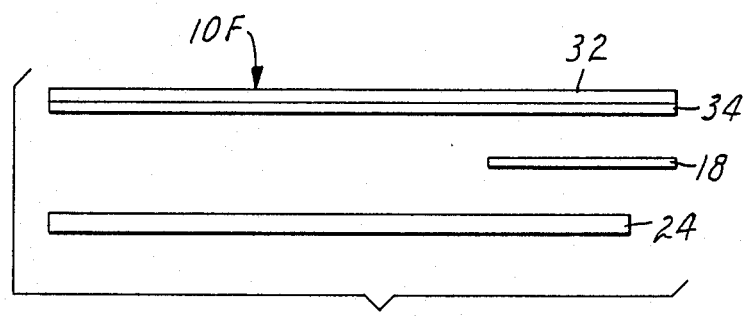

The biomedical electrode 10F illustrated in FIG. 8 is similar to the biomedical electrode 10D illustrated in FIG. 6. Biomedical electrode 10F has a top layer consisting of a protective, electrically insulative web 32 which in a preferred embodiment is an electrically insulative plastic sheet. The bottom side of protective web 32 is coated with an electrically conductive metallic coating 34 which in a preferred embodiment is aluminum which has been vapor coated onto the protective web 32 preferably in thicknesses of from 700 to 1200 angstroms. A release liner 18 with the release agent facing downward is positioned adjacent to the metallic coating 34 and covers a portion of the surface area of the biomedical electrode 10F. An electrically conductive adhesive 24 of the same type as described in FIG. 2 is then located below release liner 18 and is directly attached to release liner 18 or metallic coating 34. In use, biomedical electrode 10F may be applied to the body by electrically conductive adhesive 24. Release liner 18 may be removed and an electrical lead wire (not shown) may be inserted in place of the release liner 18. Once the electrical lead wire is placed, the protective web 32 may be resecured over the top of the electrical lead wire. Electrically conductive adhesive 24 holds both the electrical lead wire and protective web 32 in place. Metallic coating 34 over the lower surface of protective web 32 helps distribute the electrical current supplied from or to the electrical lead wire over the entire surface area of biomedical electrode 10F. In a preferred embodiment, protective web 32 with metallic coating 34 and release liner 18 extend beyond one edge of electrically conductive adhesive 24 so that they may be easily grasped to facilitate easy removal of release liner 18 when required.

Although biomedical electrode 10 has been illustrated as being in generally rectangular shaped it is to be recognized and understood that any suitable shape, size or configuration of biomedical electrode 10 may be utilized to fit or suit the particular environment or body part to which it is adapted to be applied.

Figure 9:
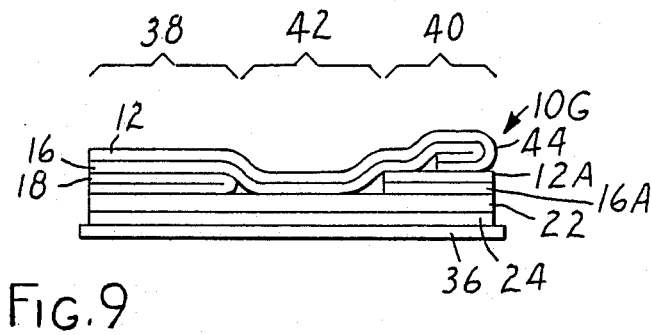
FIG. 9 is a side view of an embodiment of the biomedical electrode of the present invention.
Figure 10:
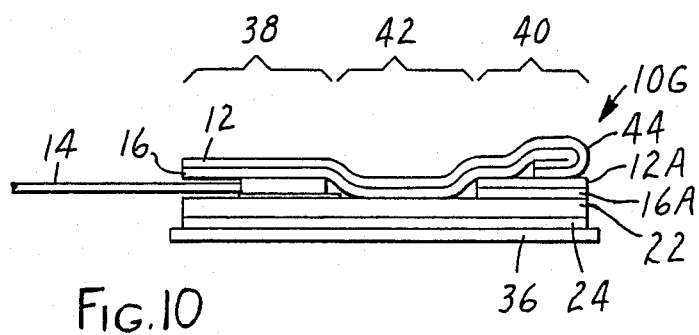
FIG. 10 is a side view of the biomedical electrode as in FIG. 9 with the electrical lead wire installed.

FIGS. 9 and 10 illustrate a side view of a biomedical electrode 10G constructed in accordance with the present invention. As in the biomedical electrode 10 disclosed in FIGS. 1, 2 and 3 and biomedical electrode 10B illustrated in FIG. 4, the biomedical electrode 10G and FIGS. 9 and 10 has a protective, electrically insulative web 12. An adhesive 16 secures the protective, electrically insulative web 12 to a conductive film 22. An electrically conductive adhesive 24 is applied to the opposite side of the conductive film 22 and itself is protected by an optional release liner 36. Release liner 36 protects the electrically conductive adhesive 24 until the electrode is to be applied to a body (not shown). A removable release liner 18 is positioned between adhesive 16 and electrically conductive film 22 to prevent the protective, electrically insulative web 12 from sticking to the electrically conductive film 22 in a first zone 38 of the biomedical electrode 10G. After the biomedical electrode 10G is applied to a body, removable release liner 18 may be removed and an electrical lead wire 14 may be inserted in the first zone 38 and secured by adhesive 16 as protective, electrically insulative web 12 is placed back over the electrical lead wire 14.

In this configuration, the biomedical electrode, 10G is suitable for use in its normal mode of operation. The electrical signals may be applied via electrical lead wire 14 to the biomedical electrode 10G which are then transmitted by the biomedical electrode 10G through electrically conductive adhesive 24 to the body or, alternative electrical signals from the body may be read by way of the biomedical electrode 10G via a connection to electrical lead wire 14. In this configuration of the biomedical electrode after a protective, electrically insulative web 12 is secured over electrical lead wire 14, there is no longer a readily available mechanism for grasping the protective, electrically insulative web 12 in order to remove the protective, electrically insulative web 12 from the remainder of the biomedical electrode 10G. Upon completion of normal use of biomedical electrode 10G, it is highly desirable to reuse electrical lead wire 14 since the cost of the electrical lead wire 14 may be many times that of the remainder of the biomedical electrode 10G. Since the electrical lead wire 14 is secured within biomedical electrode 10G by adhesive 16, it is extremely difficult, if not impossible, to remove electrical lead wire 14 as long as it is so secured. It is necessary, in most incidences, to remove protective, electrically insulative web 12 in order to release adhesive 16 from the securing of electrical lead wire 14 in the biomedical electrode 10G.

This is accomplished in the present invention by having a second zone 40 and a third zone 42, preferably intermediate the first zone 38 and the second zone 40 of the biomedical electrode 10G. In the first zone 38 of the biomedical electrode 10G, protective, electrically insulative web 12 is prevented from being secured to electrically conductive film 22 by the removable release liner 18. In the third zone 42 of the biomedical electrode 10G, the protective, electrically insulative web 12 is secured by adhesive 16 to the electrically conductive film 22. In a second zone 40 of the biomedical electrode 10G, a provision is made in an edge of protective, electrically insulative web 12 to allow the protective, electrically insulative web to be easily grasped so that the protective, electrically insulative web 12 maybe pulled and removed from the remainder of the biomedical electrode 10G resulting in the easy removal of electrical lead wire 14 from the remainder of the biomedical electrode 10G. Electrical lead wire 14 may then be reused in another biomedical electrode 10G. It is preferred that second zone 40, as illustrated in FIGS. 9 and 10, be located opposite the first zone 38 of the biomedical electrode 10G. So positioned the release liner 18 would be removed and the electrical lead wire 14 be inserted on one side of the biomedical electrode 10G and the electrical lead wire 14 would be removed by grasping the protective, electrically insulative web 12 starting from the opposite side of the biomedical electrode 10G. It is to be recognized and understood, however, that second zone 40 maybe positioned differently with respect to first the zone 38 and may even be positioned nearest the edge of the biomedical electrode 10G that the removable release liner 18 faces. It is necessary that an edge 44 be provided which can be easily grasped.

In an embodiment edge 44 may spaced from the perimeter of biomedical electrode 10G or it may be otherwise desirable to have a separate portion of the protective, electrically insulative web 12A and its associated layer of adhesive 16A in the second zone 40 in order permit even easier grasping of edge 44, as illustrated in FIGS. 9 and 10.

Figure 11:
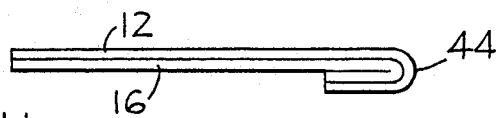
FIGS. 11, 12 and 13 illustrate side views of alternative embodiments of constructing the edge which can be grasped.
Figure 12:
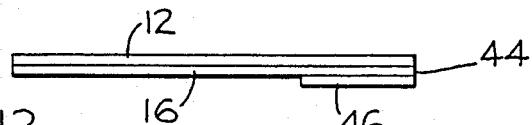
Figure 13:
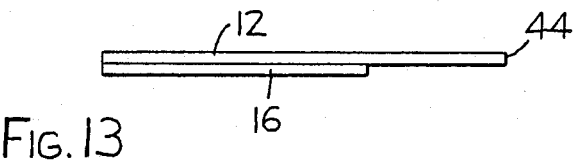

FIGS. 11, 12 and 13 show three different mechanisms in which the edge 44 which may be easily grasped may be constructed. In one embodiment of the present invention, edge 44 is formed by folding protective, electrically insulative web 12 over onto itself thus covering adhesive 16 with the protective, electrically insulative web 12. This will allow an edge 44 which is not adhesively stuck to electrically conductive film 22 to be easily grasped. This mechanism for forming edge of 44 is that mechanism illustrates in FIGS. 9 and 10. FIG. 12 illustrates that edge 44 may be formed along a portion of protective, electrically insulative web 12 by covering electrically adhesive 16 with a separate piece 46 of nonadhesive material such as another short piece of the same material from which protective, electrically insulative web 12 is constructed. In another embodiment of the present invention, illustrated in FIG. 13, edge 44 is formed by zone coating protective, electrically insulative web 12 with adhesive 16 allowing a section of protective, electrically insulative web 12 at edge 44 which is not covered by adhesive 16.

Figure 14:
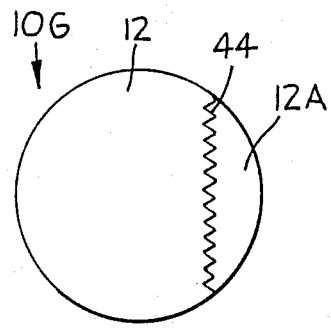
FIGS. 14 and 15 are top views of alternative embodiments of the biomedical electrode of the present invention which illustrate two variations of a scalloped edge.
Figure 15:
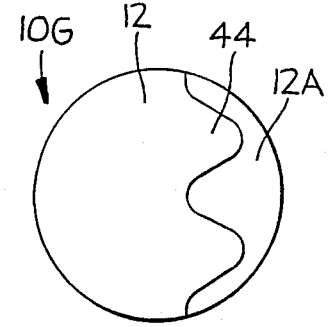

FIGS. 14 and 15 illustrate slightly alternative embodiments of biomedical electrode 10G in which edge 44 is formed by making a scalloped edge of protective, electrically insulative web 12. Scalloped edge 44 would then slightly cover a separate piece of protective, electrically insulative web 12A allowing the entire top surface of biomedical electrode 10G to be covered with protective, electrically insulative web 12 or 12A but also allowing easily grasped edge 44. As shown in FIG. 14, the scalloped edge 44 may be relatively small scallops and as shown in FIG. 15 scalloped edge 44 may be formed with relatively large scallops.

What is claimed is:

1. A biomedical electrode adapted to be applied to a body, said electrode having a surface area divided into a first zone, a second zone, and a third zone, comprising:
   a first layer of adhesive which is electrically conductive and which is adapted to be applied to said body;
   an electrically conductive layer positioned adjacent said first layer of adhesive;
   a second layer of adhesive;
   a protective, electrically insulative web positioned adjacent said second layer of adhesive;
   said second layer of adhesive holding said protective, electrically insulative web to said electrically conductive layer opposite of said first layer of adhesive in said third zone of said electrode;
   a removable release liner positioned in said first zone between said second layer of adhesive and said conductive layer preventing said protective, electrically insulative web from sticking to said electrically conductive layer in said first zone of said electrode; and
   an insertable electrical lead wire having a distal uninsulated portion and a proximate insulated portion, said distal uninsulated portion of said electrical lead wire being insertable in said first zone between said second layer of adhesive and said electrically conductive layer upon removal of said removable liner;
   said protective, electrically insulative web having an edge in said second zone, being easily grasped so that said protective, electrically insulative web may be pulled and removed from said electrode allowing removal of said electrical lead wire;
   said third zone being located intermediate said first zone and said second zone;
   said edge being formed by having a portion of said protective, electrically insulative web uncoated by said second layer of adhesive;
   said edge being spaced from the outside perimeter of said electrode.

2. A biomedical electrode as in claim 1 wherein said edge is scalloped to permit easier grasping.

3. A biomedical electrode adapted to be applied to a body, said electrode having a surface area divided into a first zone, a second zone, and a third zone, comprising:
   a first layer of adhesive which is electrically conductive and which is adapted to be applied to said body;
   an electrically conductive layer positioned adjacent said first layer of adhesive;
   a second layer of adhesive;
   a protective, electrically insulative web positioned adjacent said second layer of adhesive;
   said second layer of adhesive holding said protective, electrically insulative web to said electrically conductive layer opposite of said first layer of adhesive in said third zone of said electrode;
   a removable release liner positioned in said first zone between said second layer of adhesive and said conductive layer preventing said protective, electrically insulative web from sticking to said electrically conductive layer in said first zone of said electrode; and
   an insertable electrical lead wire having a distal uninsulated portion and a proximate insulated portion, said distal uninsulated portion of said electrical lead wire being insertable in said first zone between said second layer of adhesive and said electrically conductive layer upon removal of said removable liner;
   said protective, electrically insulative web having an edge in said second zone, being easily grasped so that said protective, electrically insulative web may be pulled and removed from said electrode allowing removal of said electrical lead wire;
   said third zone being located intermediate said first zone and said second zone;
   a portion of said protective, electrically insulative web forming said edge by being folded over in said second zone in said electrode.

4. A biomedical electrode adapted to be applied to a body, comprising:
   a first layer of adhesive which is electrically conductive and which is adapted to be applied to said body;
   an electrically conductive layer positioned adjacent said first layer of adhesive;
   a second layer of adhesive;
   a protective, electrically insulative web positioned adjacent said second layer of adhesive;
   said second layer of adhesive holding said protective, electrically insulative web to said electrically conductive layer opposite from said first layer of adhesive;
   a removable release liner positioned over a portion of the surface area of said medical electrode between said second layer of adhesive and said electrically conductive layer preventing said protective, electrically insulative web from sticking to said electrically conductive layer over said portion of the surface area of said electrode; and
   an electrical lead wire having a distal uninsulated portion and a proximate insulated portion, said distal uninsulated portion of said second electrical lead wire being inserted between said second layer of adhesive and said electrically conductive layer upon removal of said removable liner;
   said protective, electrically insulative web having an edge being easily grasped so that said protective, electrically insulative web may be pulled and removed from said electrode allowing removal of said electrical lead wire;

said edge being formed by having a portion of said protective, electrically insulative web uncoated by said second layer of adhesive;

said edge being spaced from the outside perimeter of said electrode.

5. A biomedical electrode as in claim 4 wherein said edge is scalloped to permit easier grasping.

6. A biomedical electrode adapted to be applied to a body, comprising:

a first layer of adhesive which is electrically conductive and which is adapted to be applied to said body;

an electrically conductive layer positioned adjacent said first layer of adhesive;

a second layer of adhesive;

a protective, electrically insulative web positioned adjacent said second layer of adhesive;

said second layer of adhesive holding said protective, electrically insulative web to said electrically conductive layer opposite from said first layer of adhesive;

a removable release liner positioned over a portion of the surface area of said medical electrode between said second layer of adhesive and said electrically conductive layer preventing said protective, electrically insulative web from sticking to said electrically conductive layer over said portion of the surface area of said electrode; and an electrical lead wire having a distal uninsulated portion and a proximate insulated portion, said distal uninsulated portion of said second electrical lead wire being inserted between said second layer of adhesive and said electrically conductive layer upon removal of said removable liner;

said protective, electrically insulative web having an edge being easily grasped so that said protective, electrically insulative web may be pulled and removed from said electrode allowing removal of said electrical lead wire;

a portion of said protective, electrically insulative web forming said edge by being folded over.

* * * * *